United States Patent
Roselle et al.

(10) Patent No.: US 6,867,233 B2
(45) Date of Patent: Mar. 15, 2005

(54) ACIDIC ANTIMICROBIAL COMPOSITIONS FOR TREATING FOOD AND FOOD CONTACT SURFACES AND METHODS OF USE THEREOF

(75) Inventors: Brian Joseph Roselle, Fairfield, OH (US); Fernando Ray Tollens, Indian Hill, OH (US); David Kent Rollins, Cincinnati, OH (US); Gregory Leo Jervier, Cincinnati, OH (US); Rodolfo Delgado, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 189 days.

(21) Appl. No.: 09/794,679

(22) Filed: Feb. 27, 2001

(65) Prior Publication Data

US 2001/0046979 A1 Nov. 29, 2001

Related U.S. Application Data

(60) Provisional application No. 60/185,676, filed on Feb. 28, 2000.

(51) Int. Cl.$^7$ .......................... A01N 37/00; A01N 37/44; A61K 31/195
(52) U.S. Cl. .................. 514/557; 514/568; 514/574; 514/561
(58) Field of Search .............................. 514/557, 568, 514/574, 561, 160

(56) References Cited

U.S. PATENT DOCUMENTS

| | | | |
|---|---|---|---|
| 4,336,273 A | | 6/1982 | Lee |
| 4,356,100 A | * | 10/1982 | Sherman .................. 252/106 |
| 4,404,040 A | | 9/1983 | Wang |
| 4,442,125 A | | 4/1984 | Thiele |
| 4,592,892 A | | 6/1986 | Ueno et al. |
| 4,664,014 A | * | 2/1987 | Thomson et al. ............ 521/68 |
| 4,715,980 A | | 12/1987 | Lopes et al. |
| 4,808,330 A | | 2/1989 | Chung |
| 4,818,549 A | | 4/1989 | Steiner et al. |
| 4,857,345 A | | 8/1989 | Sardo |
| 4,937,085 A | | 6/1990 | Cherry et al. |
| 4,975,217 A | | 12/1990 | Brown-Skrobot et al. |
| 4,988,522 A | | 1/1991 | Warren |
| 4,988,523 A | | 1/1991 | Gardner et al. |
| 5,075,026 A | | 12/1991 | Loth et al. |
| 5,122,541 A | | 6/1992 | Eggensberger et al. |
| 5,143,720 A | | 9/1992 | Lopes |
| 5,162,127 A | | 11/1992 | Weiss et al. |
| 5,244,666 A | * | 9/1993 | Murley .................. 424/405 |
| 5,280,042 A | | 1/1994 | Lopes |
| 5,320,772 A | | 6/1994 | Tricca |
| 5,336,500 A | * | 8/1994 | Richter et al. ............ 424/404 |
| 5,342,630 A | | 8/1994 | Jones |
| 5,346,712 A | | 9/1994 | Cherry et al. |
| 5,366,995 A | | 11/1994 | Savage et al. |
| 5,376,391 A | | 12/1994 | Nisperos-Carriedo et al. |
| 5,389,389 A | | 2/1995 | Beck |
| 5,460,833 A | | 10/1995 | Andrews et al. |
| 5,490,992 A | | 2/1996 | Andrews et al. |
| 5,834,413 A | * | 11/1998 | Durbut et al. ............ 510/365 |
| 5,942,478 A | | 8/1999 | Lopes |
| 5,945,146 A | | 8/1999 | Twinam |
| 6,228,821 B1 | * | 5/2001 | Sliva ..................... 510/101 |
| 6,699,828 B1 | * | 3/2004 | de Buzzaccarini et al. . 510/372 |

FOREIGN PATENT DOCUMENTS

| | | | |
|---|---|---|---|
| CA | 1 166 547 | | 5/1984 |
| CA | 2 096 837 | | 5/1992 |
| CA | 2 267 678 | | 4/1998 |
| GB | 917432 | | 2/1963 |
| JP | 81010606 | * | 3/1981 |
| JP | 57048712 | * | 3/1982 |
| JP | 03009997 | * | 1/1991 |

* cited by examiner

Primary Examiner—Alton Pryor
(74) Attorney, Agent, or Firm—Jason J. Camp; Jeffrey V. Bamber; Brent M. Peebles

(57) ABSTRACT

Acidic antimicrobial compositions for treating food surfaces and food contact surfaces comprise an organic acid and a surfactant, said composition having a pH of from about 2 to about 5. Concentrated, acidic antimicrobial compositions preferably comprise a stabilizing agent to prevent precipitation of the surfactant upon dilution of the concentrated composition. Methods of use comprise contacting food surfaces or food contact surfaces with the compositions of the present invention. Articles of manufacture comprise a container, an acidic antimicrobial composition, and a set of instructions in association with the container.

10 Claims, No Drawings

ACIDIC ANTIMICROBIAL COMPOSITIONS FOR TREATING FOOD AND FOOD CONTACT SURFACES AND METHODS OF USE THEREOF

CROSS-REFERENCE TO RELATED APPLICATION

This patent application claims the benefit of U.S. Provisional Application Ser. No. 60/185,676 filed Feb. 28, 2000, by Brian J. Roselle et al., which is incorporated by reference herein.

TECHNICAL FIELD

The present invention relates to methods for cleaning surfaces and reducing microorganisms, especially for the purpose of making food, more especially produce, more safe for human consumption, and to compositions, especially in concentrated, or the corresponding diluted liquid form, which are especially suitable for practicing said methods.

BACKGROUND OF THE INVENTION

Fruits and vegetables, food contact surfaces, and sometimes other food products such as meats, are desirably washed prior to ingestion in order to remove soils and other unwanted residues which may be undesirably clinging to the surfaces thereof. It is also desirable to reduce microorganisms on food and food contact surfaces, thus ensuring safety.

It is especially desirable to provide effective, toxicologically-acceptable compositions for treating food, including fruits and vegetables and/or meats, that can be sold in concentrated form and used to create dilute, low-sudsing liquid solutions which can be used to effect antimicrobial action and which desirably provide palatable food without removal of the composition. Dilute liquid solutions are convenient for the user, since they can be applied directly to soiled fruits and vegetables, or by simple immersion of the soiled food items in the solution, thus ensuring that all parts of the food items are treated. Clarity of the dilute liquids connotes cleanliness to the user and is thus highly desirable. Low-sudsing is an important attribute so that the elimination of any suds is achieved quickly and easily. It is also of advantage if such concentrates can be diluted by the consumer using water that is not generally safe for use, since that is sometimes the only water that is available.

SUMMARY OF THE INVENTION

The present invention encompasses compositions, articles of manufacture, and methods for treating surfaces, such as food, including produce, especially fruits and vegetables, (and compositions, as disclosed hereinafter, for practicing said methods), and food contact surfaces, at an acidic pH, even without rinsing, to effect microorganism reduction in a short time period, preferably less than about 1 minute, especially while maintaining palatability of the treated food. In its broadest aspect, the present invention comprises a method for treating food to reduce the level of microorganisms on the food item, said treatment preferably occurring just prior to consumption, comprising the step of contacting the surface of said food item with an acidic antimicrobial composition comprising (1) organic acid; (2) surfactant, preferably selected from the group consisting of anionic surfactant, nonionic surfactant, and mixtures thereof, and preferably at a level of at least about 0.003% by weight of the composition; and (3) optionally, a stabilizing agent; preferably for a period of time of at least about 15 seconds, the composition preferably being essentially free of any material that adversely affects palatability so that said food does not need to be rinsed before consumption.

The present invention also relates to more specific methods including a method for rendering food, including produce and/or meat, safe to eat comprising contacting the surfaces of said food, shortly before ingestion so as to minimize the chances for recontamination, by direct application of a dilute aqueous treatment composition having an acidic pH below about 5.0, said composition typically comprising:

(a) an effective amount, to kill and/or reduce microorganisms on the treated surface, preferably a food surface or food contact surface, of an acid, preferably an organic acid selected from the group consisting of citric acid, lactic acid, malic acid, salicylic acid, acetic acid, adipic acid, fumaric acid, hydroxyacetic acid, dehydroacetic acid, glutaric acid, tartaric acid, fumaric acid, succinic acid, propionic acid, aconitic acid, sorbic acid, benzoic acid, gluconic acid, ascorbic acid, alanine, lysine, and mixtures thereof, the level of organic acid preferably being at least about 0.003%, more preferably at least about 0.02%, and still more preferably at least about 0.03%, by weight of the dilute aqueous treatment composition;

(b) at least about 0.003%, preferably less than about 5%, more preferably less than about 2%, and even more preferably less than about 1%, by weight of surfactant preferably selected from the group consisting of anionic surfactant, nonionic surfactant, and mixtures thereof; and preferably a $C_{6-18}$ alkyl sulfate, sulfonate, and/or soap, more preferably a $C_{12}$ alkyl sulfate such as sodium lauryl sulfate, and preferably in an amount sufficient to reduce the surface tension and to maintain the viscosity to less than about 50 centipoise ("cP"), preferably to less than about 10 cP, and more preferably to less than about 5 cP, to help maximize surface wetting and/or drainage thus minimizing residue, but preferably less than an amount that will affect palatability, of toxicologically-acceptable detergent surfactant;

(c) an effective amount, to help stabilize the solution interfacial tension or prevent precipitation of said surfactant, of a stabilizing agent, preferably selected from the group consisting of organic nonionic and polymeric adjuncts, salts, and mixtures thereof; and preferably at level of from about 0.0002% to about 3.5%, more preferably from about 0.0005% to about 2.75%, and still more preferably from about 0.001% to about 1%, by weight of the dilute aqueous treatment composition;

(d) optionally, an effective amount, to maintain the pH of the composition, of a buffer, preferably a toxicologically-acceptable organic acid salt buffer, and preferably selected from the group consisting of the sodium, potassium, magnesium, ammonium salts of citric acid and mixtures thereof; and preferably at a level of from about 0.0005% to about 3%, more preferably from about 0.0015% to about 1.5%, and still more preferably from about 0.0025% to about 0.75%, by weight of the dilute aqueous treatment composition;

(e) optionally, toxicologically-acceptable anti-foaming agent;

(f) optionally, toxicologically-acceptable preservative;

(g) optionally, perfume, flavoring agent, and/or coloring agent; and (h) the balance comprising an aqueous carrier comprising water and, optionally, low levels of low molecular weight, toxicologically-acceptable organic solvent such as ethanol, glycerol, etc. and/or minor ingredients; the dilute aqueous treatment composition having a pH of from about 2 to about 5, preferably from about 2.3 to about 3.5, and more preferably from about 2.5 to about 3.2; and said composition being essentially free of any material that is not toxicologically acceptable, said composition being able to effect at least a one log reduction of targeted micro-organisms in less than about 1 minute, optionally followed by draining and/or drying said composition from said food, even without rinsing said food, said food being then ready for consumption and having desirable palatability.

The present invention also encompasses concentrated, acidic antimicrobial compositions, preferably powdered anhydrous compositions, suitable for use in preparing such dilute compositions for treating food at an acidic pH below about 5.0, by diluting with water to form a dilute aqueous treatment composition using from about 0.05% to about 5%, preferably from about 0.2% to about 3%, of the concentrated composition, by weight of the dilute aqueous treatment composition, said concentrated, acidic antimicrobial composition comprising:

(a) from about 5% to about 95%, preferably from about 30% to about 85%, and more preferably from about 60% to about 80%, by weight of said concentrated composition, of an acid, preferably an organic acid selected from the group consisting of citric acid, lactic acid, malic acid, salicylic acid, acetic acid, adipic acid, fumaric acid, hydroxyacetic acid, dehydroacetic acid, glutaric acid, tartaric acid, fumaric acid, succinic acid, propionic acid, aconitic acid, sorbic acid, benzoic acid, gluconic acid, ascorbic acid, alanine, lysine, and mixtures thereof;

(b) from about 1% to about 80%, preferably from about 4% to about 25%, and more preferably from about 6% to about 15%, by weight of said concentrated composition, of surfactant preferably selected from the group consisting of anionic surfactant, nonionic surfactant, acid-sensitive amphoteric surfactants, and mixtures thereof; and preferably a $C_{6-18}$ alkyl sulfate, sulfonate, more preferably a $C_{12}$ alkyl sulfate such as sodium lauryl sulfate;

(c) from about 0.25% to about 70%, preferably from about 1% to about 55%, and more preferably from about 2% to about 20%, by weight of said concentrated composition, of a stabilizing agent, preferably selected from the group consisting of organic nonionic and polymeric adjuncts, salts, and mixtures thereof;

(d) optionally, an effective amount, to maintain the pH of the composition, of a buffer, preferably a toxicologically-acceptable organic acid salt buffer, or for powders preferably selected from the group consisting of sodium carbonate, sodium bicarbonate, magnesium carbonate hydroxide, and mixtures thereof; and preferably at a level of from about 1% to about 60%, more preferably from about 3% to about 30%, and still more preferably from about 5% to about 15%, by weight of said concentrated composition;

(e) optionally, toxicologically-acceptable anti-foaming agent;

(f) optionally, toxicologically-acceptable preservative;

(g) optionally, perfume, flavoring agent, and/or coloring agent; and (h) the balance comprising compatible, toxicologically-acceptable inert and/or minor ingredients.

In all of the above lists of components, if an ingredient can be classified in more than one place, it will be classified in the first place it can appear. Preferably all ingredients are food grade, more preferably "generally recognized as safe" ("GRAS"), since they may be ingested.

The present invention also relates to articles of manufacture for cleaning surfaces, especially food surfaces or food contact surfaces, comprising (1) a container, (2) an acidic antimicrobial composition comprising an organic acid and surfactant, and (3) a set of instructions.

The present invention further relates to methods of promoting the sale of food items, especially produce such as fruits or vegetables, comprising the steps of contacting said food items with an acidic antimicrobial composition comprising an organic acid and surfactant and providing informational indicia in association with said food items to indicate/communicate to a consumer of said food item that said food item has been treated with said acidic antimicrobial composition.

All documents cited herein are incorporated herein by reference, unless otherwise specified.

DETAILED DESCRIPTION OF THE INVENTION

The present invention relates to an acidic antimicrobial composition for cleaning a surface and/or killing or reducing microorganisms on a surface, especially foods and food contact surfaces, said compositions comprising an organic acid, surfactant, preferably an anionic surfactant, and a stabilizing agent. The present invention especially relates to concentrated, acidic antimicrobial compositions that are dilutable to form dilute aqueous treatment compositions. The present invention further encompasses methods of using acidic antimicrobial compositions comprising organic acid and surfactant, and articles of manufacture containing such compositions.

The present invention encompasses compositions, articles of manufacture, and methods for treating surfaces, such as food, including produce, especially fruits and vegetables, (and compositions, as disclosed hereinafter, for practicing said methods), and food contact surfaces, at an acidic pH, even without rinsing, to effect microorganism reduction in a short time period, preferably less than about 1 minute, especially while maintaining palatability of the treated food. In its broadest aspect, the present invention comprises a method for treating food to reduce the level of microorganisms on the food item, said treatment preferably occurring just prior to consumption, comprising the step of contacting the surface of said food item with an acidic antimicrobial composition comprising (1) organic acid; (2) surfactant, preferably selected from the group consisting of anionic surfactant, nonionic surfactant, and mixtures thereof, and preferably at a level of at least about 0.003% by weight of the composition; and (3) optionally, a stabilizing agent; preferably for a period of time of at least about 15 seconds, the composition preferably being limited in material that adversely affects palatability so that said food does not need to be rinsed before consumption.

The present invention also relates to more specific methods including a method for rendering food, including produce and/or meat, safe to eat comprising contacting the surfaces of said food, shortly before ingestion so as to minimize the chances for recontamination, by direct application of a dilute aqueous treatment composition having an acidic pH below about 5.0, said composition typically comprising:

(a) an effective amount, to kill and/or reduce microorganisms on the treated surface, preferably a food surface or food contact surface, of an acid, preferably an organic acid selected from the group consisting of citric acid, lactic acid, malic acid, salicylic acid, acetic acid, adipic acid, fumaric acid, hydroxyacetic acid, dehydroacetic acid, glutaric acid, tartaric acid, fumaric acid, succinic acid, propionic acid, aconitic acid, sorbic acid, benzoic acid, gluconic acid, ascorbic acid, alanine, lysine, and mixtures thereof, the level of organic acid preferably being at least about 0.0025%, more preferably at least about 0.015%, and still more preferably at least about 0.03%, by weight of the dilute aqueous treatment composition;

(b) at least about 0.003%, preferably less than about 5%, more preferably less than about 2%, and even more preferably less than about 1%, by weight of surfactant preferably selected from the group consisting of anionic surfactant, nonionic surfactant, acid sensitive amphoteric surfactant, and mixtures thereof; and preferably a $C_{6-18}$ alkyl sulfate, sulfonate, more preferably a $C_{12}$ alkyl sulfate such as sodium lauryl sulfate, and preferably in an amount sufficient to reduce the surface tension and to maintain the viscosity to less than about 50 centipoise ("cP"), preferably to less than about 10 cP, and more preferably to less than about 5 cP, to help maximize surface wetting and/or drainage thus minimizing residue, but preferably less than an amount that will affect palatability, of toxicologically-acceptable detergent surfactant;

(c) an effective amount, to help stabilize the solution interfacial tension or prevent precipitation of said surfactant, of a stabilizing agent, preferably selected from the group consisting of organic nonionic and polymeric adjuncts, salts, and mixtures thereof; and preferably at level of from about 0.0002% to about 3.5%, more preferably from about 0.0005% to about 2.75%, and still more preferably from about 0.001% to about 1%, by weight of the dilute aqueous treatment composition;

(d) optionally, an effective amount, to maintain the pH of the composition, of an buffer, preferably a toxicologically-acceptable organic acid salt buffer, and preferably from a powder formed from the selected from the group consisting of sodium carbonate, sodium bicarbonate, magnesium carbonate hydroxide, and mixtures thereof; and preferably at a level of from about 0.0005% to about 3%, more preferably from about 0.0015% to about 1.5%, and still more preferably from about 0.0025% to about 0.75%, by weight of the dilute aqueous treatment composition;

(e) optionally, toxicologically-acceptable anti-foaming agent;

(f) optionally, toxicologically-acceptable preservative;

(g) optionally, perfume, flavoring agent, and/or coloring agent; and (h) the balance comprising an aqueous carrier comprising water and, optionally, low levels of low molecular weight, toxicologically-acceptable organic solvent such as ethanol, glycerol, etc. and/or minor ingredients;

the dilute aqueous treatment composition having a pH of from about 2 to about 5, preferably from about 2.3 to about 3.5, and more preferably from about 2.5 to about 3.2; and said composition being essentially free of any material that is not toxicologically acceptable, said composition being able to effect at least a one log reduction of targeted micro-organisms in less than about 5 minutes, optionally followed by draining and/or drying said composition from said food, even without rinsing said food, said food being then ready for consumption and having desirable palatability.

The present invention also encompasses concentrated, acidic antimicrobial compositions, preferably powdered dry compositions, suitable for use in preparing such dilute compositions for treating food at an acidic pH below about 5.0, by diluting with water to form a dilute aqueous treatment composition using from about 0.05% to about 5%, preferably from about 0.01% to about 1%, of the concentrated composition, by weight of the dilute aqueous treatment composition, said concentrated, acidic antimicrobial composition comprising:

(a) from about 5% to about 95%, preferably from about 30% to about 85%, and more preferably from about 60% to about 80%, by weight of said concentrated composition, of an acid, preferably an organic acid selected from the group consisting of citric acid, lactic acid, malic acid, salicylic acid, acetic acid, adipic acid, fumaric acid, hydroxyacetic acid, dehydroacetic acid, glutaric acid, tartaric acid, fumaric acid, succinic acid, propionic acid, aconitic acid, sorbic acid, benzoic acid, gluconic acid, ascorbic acid, alanine, lysine, and mixtures thereof;

(b) from about 1% to about 80%, preferably from about 4% to about 25%, and more preferably from about 6% to about 15%, by weight of said concentrated composition, of surfactant preferably selected from the group consisting of anionic surfactant, nonionic surfactant, acid-sensitive amphoteric surfactant and mixtures thereof; and preferably a $C_{6-18}$ alkyl sulfate, sulfonate, more preferably a $C_{12}$ alkyl sulfate such as sodium lauryl sulfate;

(c) from about 0.25% to about 70%, preferably from about 1% to about 55%, and more preferably from about 2% to about 20%, by weight of said concentrated composition, of a stabilizing agent, preferably selected from the group consisting of organic nonionic and polymeric adjuncts, salts, and mixtures thereof;

(d) optionally, an effective amount, to maintain the pH of the composition, of an buffer, preferably a toxicologically-acceptable organic acid salt buffer, or for powders preferably selected from the group consisting of sodium carbonate, sodium bicarbonate, magnesium carbonate hydroxide, and mixtures thereof; and preferably at a level of from about 1% to about 60%, more preferably from about 3% to about 30%, and still more preferably from about 5% to about 15%, by weight of said concentrated composition;

(e) optionally, toxicologically-acceptable anti-foaming agent;

(f) optionally, toxicologically-acceptable preservative;

(g) optionally, perfume, flavoring agent, and/or coloring agent; and (h) the balance comprising compatible, toxicologically-acceptable inert and/or minor ingredients.

In all of the above lists of components, if an ingredient can be classified in more than one place, it will be classified in the first place it can appear. Preferably all ingredients are food grade, more preferably "generally recognized as safe" ("GRAS"), since they may be ingested.

A more specific method for preparing food, especially produce such as fruits and vegetables involves exposing the food to a dilute aqueous solution having a acidic pH of less than about 5 as described above, for a period of time of up to about 5 minutes.

An acidic method for treating food can comprise contacting the surfaces of produce with an aqueous solution prepared by creating a solution having a pH of from about 2 to about 5, preferably from about 2.3 to about 3.5, more preferably from about 2.5 to about 3.2, using the concentrated composition above and impure water, to provide pure solutions that kill microorganisms on the surface of food. It is important to reduce the level of microorganisms on the surface of food.

Another preferred variation in the above methods for treating food such as produce involves placing concentrated compositions, as disclosed herein, into containers in association with instructions to use the composition to form said dilute solutions to treat food. Such instructions are very important, since the amount of dilution, the time of treatment, special instructions regarding rinsing, and the ability to use impure water to form the treatment solution are not intuitive. It is also important that the instructions be as simple and clear as possible, so that using pictures and/or icons is desirable.

The balance of the composition can comprise various optional adjunct materials, pH-adjusting agents, perfumes or essences, preservatives, suds suppressors, and the like.

The ingredients in the above concentrated compositions are preferably "food grade" and selected and used in proportions which provide substantially clear dilute compositions. "Substantially clear" includes only minimal precipitation, and preferably the compositions are "completely clear" meaning no precipitation of ingredients out of solution. The ingredients are also selected to have minimal odor, both initially and after storage. The lack of objectionable odor is especially important in compositions for use on food.

In order to mask any objectionable odor, the compositions can contain a food grade or GRAS (defined hereinafter) perfume, or essence, ingredient. Especially preferred for this use are oils derived from citrus fruit, e.g., oranges, lemons, limes, grapefruits, tangerines, tangelos, etc. which contain relatively large amounts of terpenes.

Preferred compositions for use herein contain only materials that are food grade or GRAS, including, of course, direct food additives affirmed as GRAS, to protect against possible misuse by the consumer. Traditionally, most suggestions for cleaning of fruits and/or vegetables have contemplated a commercial scale where there is typically more control over the conditions, especially the amount and thoroughness of rinsing. The present invention includes use by individual consumers without rinsing, so that it is essential that extra safety be built into the product. Failure to rinse thoroughly after cleaning is less of a concern if all of the ingredients are GRAS and/or food grade.

The use and selection of cleaning ingredients for the purpose of washing fruits and vegetables is described by the United States Code of Federal Regulations, Title 21, Section 173.315: "Ingredients for use in washing or lye peeling of fruits and vegetables". These regulations restrict the ingredients that may be used for direct contact with food to those described as "generally recognized as safe" (GRAS), and a few other selected ingredients. These sections also provide certain limitations on the amount of material that can be used in a given context. However, there are no regulations, or suggestions, for methods of making food safe for consumption using aqueous compositions that do not need to be removed. Also, there is no known method for killing microbes using materials like hypochlorite, iodine, etc. at low levels that provide desirable palatability.

When cleaning food and food contact surfaces with aqueous acid solutions containing anionic surfactants, a preferred approach is to form a dilute aqueous treatment composition from a concentrated, acidic antimicrobial composition, preferably a powdered anhydrous composition, using any available water as the dilutant in preparing the dilute aqueous treatment composition. Addition of a stabilizing agent in the concentrated composition helps to maintain the efficacy of the acid and anionic system by retarding or eliminating ingredient precipitation and/or stabilizing solution properties such as interfacial tension. Ingredient precipitation typically can be seen visually as a separate phase which forms and settles out of solution. Stabiliziation of interfacial tension tends to be difficult to quantify, but can be observed by measuring the contact angle of the solution on a substrate.

A common problem encountered with dilution water, which can be either unsafe or safe to drink itself, is the precipitation of formula ingredients, especially anionic surfactants, from the final dilute aqueous treatment composition as a result of dissolved materials in the diluting water which are not totally compatible with the concentrated, acidic antimicrobial composition. For example, diluting water that has not been deionized can contain high levels of inorganic salts such as calcium an the like. Calcium is especially problematic in precipitating sulfate and sulfonate anionic surfactants under acidic conditions. Precipitation of active materials of the concentrated composition completely out of the dilute composition is highly undesired as it will severely limit the cleaning and antimicrobial efficiency of the solution. Partial precipitation of the actives is also undesired as it negatively effects solution cleaning and antimicrobial efficacy over time.

Preferred embodiments of the compositions of the present invention include, but are not limited to, dilutable anhydrous powder concentrates, tablets, liquid concentrates, and the like.

Variations in usage of these compositions can include non-food contact hard surfaces, as well as soft surfaces such as cloths, carpets, fabrics, and the like. As a sanitizing rinse, dilutions of the present concentrated compositions can be used for cleaning/sanitizing medical smocks, hotel/hospital linens, nurse uniforms, and the like.

Since these composition are preferably used on food and food contact surfaces, it is preferred that the ingredients be toxicologically safe to humans. This is especially important in the case where food is cleaned in the dilute aqueous treatment compositions, and post-rinsing with fresh water is not utilized. In preferred compositions, the ingredients of the present compositions have a human safety pedigree and appear on an approved list for use with food. In the United States, for example, ingredients pre-approved for food use are listed in the United States Code of Federal Regulations ("C.F.R."), Title 21. Ingredients that are pre-approved for use food are the Direct Food Additives and Generally Recognized As Safe ("GRAS") ingredients. Other ingredients that are well established as safe, or have adequate toxicological and safety pedigree, can be added to existing lists or approved via a self-GRAS affirmation process.

I. Acidic Antimicrobial Compositions

A. Organic Acid

The present invention results from the unexpected discovery that certain organic acids such as citric, malic, succinic, and benzoic, used in suitable concentrations, as further described herein, are highly efficacious against microbes, such as *Salmonella choleraesuis* and *Staphylococcus aureus*. When used in the presence of a surfactant, preferably an anionic surfactant such as sodium lauryl sulfate (for example, Empicol™ commercially available from Albright and Wilson), these acids typically have effective antimicrobial activity against a variety of microbes, including gram negative (−) bacteria, such as *Salmonella choleraesuis*, and gram positive (+) bacteria, such as *Staphylococcus aureus*.

In general, the water soluble carboxylic acids useful in accordance with the invention have the following structure:

wherein R may be represented by: lower alkyl; substituted lower alkyl; hydroxy lower alkyl (e.g. $HOCH_2$—); carboxy lower alkyl (e.g. $HOOC—CH_2—CH_2$—); carboxy, hydroxy lower alkyl (e.g., $HOOCCH_2$ CHOH—); carboxy, halo lower alkyl (e.g. $HOOCCH_2CHBr$—); carboxy, dihydroxy lower alkyl (e.g. HOOC—CHOH—CHOH—); dicarboxy, hydroxy lower alkyl (e.g. $HOOC—CH_2C—C(OH)(COOH)$ $H_2$—); lower alkenyl, carboxy lower alkenyl (e.g. HOOCCH═CH—); dicarboxy lower alkenyl (e.g. $HOOC—CH_2C(COOH)$═CH—); phenyl ($C_6$ $H_5$—); substituted phenyl (e.g. hydroxy phenyl HO—$C_6$ $H_4$—). Other acid examples include hydroxy lower alkyl e.g. lactic; carboxy, hydroxy lower alkyl, e.g. 2-methyl malic; carboxy, halo lower alkyl, e.g. 2-chloro-3-methyl succinic; carboxy, dihydroxy lower alkyl, e.g. 2-methyl tartaric; dicarboxy, hydroxy lower alkyl, e.g. 2-methyl citric acid; and carboxy lower alkenyl, e.g. fumaric. The above definitions are used in an illustrative but not a limiting sense. The term "lower" as used herein refers to an acid wherein "R" contains one to six carbon atoms. The term "substituted" indicates that one or more hydrogen atoms are substituted by halogen atoms (F, Cl, Br, I) hydroxyl groups, amino groups, thiol groups, nitro groups, cyano groups, and the like. Examples of preferred antimicrobial organic acids include, but are not limited to, citric acid, lactic acid, malic acid, maleic acid, salicylic acid, acetic acid, adipic acid, fumaric acid, hydroxyacetic acid, dehydroacetic acid, glutaric acid, tartaric acid, fumaric acid, succinic acid, propionic acid, aconitic acid, sorbic acid, benzoic acid, gluconic acid, ascorbic acid, alanine, lysine, and mixtures thereof.

In some cases, where the organic acid is derived chemically from other organic sources, it may be desirable to have the starting organic source come from a non-genetically modified organism. For example, it may be preferred that for a food wash product containing citric acid which is derived from corn starch and molasses, that the corn or beet sources are not from genetically modified hybrids. In a preferred embodiment, organic acid in the present compositions is not derived from genetically modified sources.

Some acids derived from organic acids as well as non-organic acids may also prove efficacious alone, or in conjunction with, an organic acid. Examples of these include phosphoric acid, sulfamic acid, oxalic acid.

In a preferred embodiment, the present compositions are concentrated, acidic antimicrobial compositions comprising an organic acid at a level of from about 5% to about 95%, more preferably from about 30% to about 85%, and still more preferably from about 60% to about 80% by weight of the concentrated antimicrobial composition. The level of the acid should take into consideration the other ingredients and the recommended dilution amount in order to maintain the desired solution pH. Citric acid is a highly preferred organic acid having antimicrobial action. Citric acid is preferred because it is a natural acid and is relatively safe for use on household surfaces, especially food contact surfaces, and on produce such as fruits and vegetables.

When the concentrated, acidic antimicrobial compositions are diluted to form a dilute aqueous treatment composition, the level of organic acid in the dilute aqueous treatment composition is from about 0.003% to about 4.75%, preferably from about 0.015% to about 4.25%, and more preferably from about 0.03% to about 4%, by weight of the dilute aqueous treatment composition.

B. Surfactants

1. Anionic Surfactants

Anionic surfactants can be employed, e.g., preferably approved for use on foods, such as allowed in the United States by the United States Code of Federal Regulations (CFR), Title 21. Specific mention is made of salts of dodecylbenzene sulfonate, typically at levels up to 0.2% in use, and sodium lauryl sulfate. Also described in the CFR are phosphate esters of ethylene and/or ethylene/propylene oxide adducts of aliphatic alcohols, dioctyl sulfosuccinate, 2-ethylhexyl sulfate, and mono and di-methyl naphthalene sulfonates.

The anionic surfactant is preferably selected from materials known in the art, such as $C_{6-18}$ alkyl sulfates and/or sulfonates; $C_{6-15}$ alkylbenzene sulfonates; $C_{6-18}$ alkyl ether sulfates; di-$C_{6-10}$ alkyl sulfosuccinates, and the like. The alkyl sulfates are preferred, for antimicrobial effectiveness and palatability, especially as the sodium salts. A highly preferred anionic surfactant, especially for concentrated, anhydrous powdered compositions, is sodium lauryl sulfate. Sodium and potassium $C_{8-14}$ soaps are not preferred as standalone surfactants in the acid conditions of this invention. Mixtures of such alkyl sulfates and sulfonates are also preferred.

Anionic surfactant is typically employed in concentrated compositions at levels of from about 1% to about 80%, preferably from about 4% to about 25%, and more preferably from about 6% to about 15%, by weight of the concentrated composition. In dilute aqueous treatment compositions, the level of anionic surfactant is typically from about 0.001% to about 5%, preferably from about 0.002% to about 2%, and more preferably from about 0.003% to about 1%, by weight of the dilute aqueous treatment composition.

2. Nonionic Surfactants

Nonionic surfactants, when used, are preferably selected from materials known in the art, such as alkylene oxide (ethylene oxide and/or propylene oxide) adducts of $C_{10-18}$ aliphatic alcohols or acids, polysorbates, $C_{10-18}$ aliphatic alcohol adducts of glucose (alkyl polyglucosides). The specific nonionic surfactant selected ideally has a cloud point above about 35° C. in the composition. The United States Code of Federal Regulations (CFR) specifically describes an ethylene oxide/propylene oxide adduct of C12–18 aliphatic alcohol of molecular weight of about 800. Such a material is available as PLURAFAC RA-20 (BASF).

If used in the present compositions, nonionic surfactant is employed in concentrated compositions at levels of from about 0.5% to about 40%, preferably from about 2% to about 10%, and more preferably from about 3% to about 8%, by weight of the concentrated composition. In dilute aqueous treatment compositions, the level of nonionic surfactant is typically from about 0.0002% to about 2%, preferably from about 0.001% to about 0.7%, and more preferably from about 0.002% to about 0.4%, by weight of the dilute aqueous treatment composition.

3. Acid Surfactants and Acid-Sensitive Amphoteric Surfactants

The compositions herein can contain acid surfactants like alklybenzenesulfonic acid, acid-sensitive amphoteric surfactants, and low levels of protonated fatty surfactants like lauric acid.

The detergent surfactant also is used for reduction of the surface tension and controlling viscosity. It is highly desirable that the dilute treatment compositions have a low viscosity, typically less than about 50, preferably less than about 10, and more preferably less than about 5. The low viscosity improves the completeness of the treatment by promoting spreading over the surface of the food, especially where there are layers, rugosities, etc. The low viscosity also improves drainage, thus providing at least some soil removal. Low viscosity also improves speed of drying, if that is desired. Thus, the detergent surfactant provides highly important advantages in terms of treatment.

In combination with an organic acid, such as citric acid, the detergent surfactant improves antimicrobial action. The presence of the surfactant, and especially the alkyl sulfate, provides improved kill and/or rate of kill, especially for short times and/or lower pH.

It is important that the detergent surfactant not affect palatability. Accordingly, the level should be low.

If used in the present compositions, acid surfactant and/or acid-sensitive amphoteric surfactant is employed in concentrated compositions at levels of from about 0.5% to about 40%, preferably from about 2% to about 10%, and more preferably from about 3% to about 8%, by weight of the concentrated composition. In dilute aqueous treatment compositions, the level of acid surfactant and/or acid-sensitive amphoteric surfactant is typically from about 0.0002% to about 2%, preferably from about 0.001% to about 0.7%, and more preferably from about 0.002% to about 0.4%, by weight of the dilute aqueous treatment composition.

C. Stabilizing Agent

The present compositions further comprise a stabilizing agent, organic or inorganic, preferably selected from the group consisting of selected nonionic materials, polymeric materials, electrolytes, and mixtures thereof. The stabilizing agent used herein is preferably free of calcium. The stabilizing agent, or mixture of stabilizing agents, are added at a level necessary to prevent or retard surfactant precipitation and/or to minimize changes in the solution interfacial tension over time. Nonionic materials and polymeric materials are typically more hydrophobic than the anionic surfactant and preferably added at a level less than the surfactant, or minimally to facilitate the desired stabilizing effect on the surfactant. Electrolytes, when added, are water soluble salts having a mono-, di-, or trivalent cation. Suitable electrolytes include chlorides, sulfates, nitrates, carbonates, and mixtures thereof, of sodium, ammonium, magnesium, potassium, and/or aluminum. A preferred salt is magnesium sulfate. Calcium salts are not preferred, and as mentioned above, the stabilizing agent is free of calcium. The pH effect of the salts on the final usage solution should be considered, and the salts should be added in conjunction with the acid so as not to have the final solution outside the preferred pH range.

Typical polymers and nonionic materials include polypropylene glycol, polyoxyalkylene derivatives of propylene glycol (e.g. nonionic materials commerically available under the trade name Pluronic® from BASF), polysorbates, and mixtures thereof. These stabilizing agents are highly preferred in compositions containing the preferred anionic surfactants herein, such as sodium lauryl sulfate. The stabilizing agents tend to keep surfactants in solution and prevent them from precipitating out of solution. The preferred stabilizing agent herein is polypropylene glycol.

Polypropylene glycol suitable as a stabilizing agent in the present compositions include polypropylene glycols having a solubility in deionized water less than the corresponding surfactant. The preferred molecular weights are greater than about 400. A preferred polypropylene glycol stabilizing agent is Polypropylene Glycol 2000 available from Dow Chemical.

Stabilizing agents are typically used in the present concentrated compositions at a level of from about 0.25% to about 70%, preferably from about 1% to about 55%, and more preferably from about 2% to about 20%, by weight of the concentrated composition. In dilute aqueous treatment compositions, stabilizing agents are used at levels of from about 0.0002% to about 3.5%, preferably from about 0.0005% to about 2.75%, and more preferably from about 0.001% to about 1%, by weight of the dilute aqueous treatment composition.

The present stabilizing agents function to maintain the present surfactant in solution. In the preferred concentrated, anhydrous powder compositions, the stabilizing agents act to keep surfactants from precipitating out of solution when the powdered compositions are diluted. The present stabilizing agents are preferably sufficiently hydrophobic and typically used in the present compositions at levels relative to the amount of surfactant used in the composition.

Wherein the present composition comprises both surfactant, especially an anionic surfactant, and a stabilizing agent, the stabilizing agent and surfactant are generally in a ratio of stabilizing agent to surfactant of from about 10:1 to about 1:20, preferably from about 3:1 to about 1:15, and more preferably from about 1:1 to about 1:10. In a preferred embodiment, a ratio of stabilizing agent to surfactant is about 1:3.

D. Buffer System

Toxicologically-acceptable acidic buffers are optionally, but preferably, used in the present compositions herein to maintain product pH in the desired range. For ease of formulating, it is often desirable that such acidic buffers be in their sodium salt form, especially in anhydrous, powdered concentrated compositions that utilize anionic surfactants, such as sodium lauryl sulfate. Sodium salt buffers are preferred over potassium salt in conjunction with alkyl sulfate/sulfonate surfactants like sodium alkyl sulfate and sodium alklybenzesulfonate. When using organic acids to achive the acidic pH, it is often convenient to have a salt of the acid serve as a buffering compound. For example, sodium citrate can be used in conjunction with citric acid. This approach also lends itself to the formation of the buffer in-situ when a more alkaline salt is included with the acid such that when a solution is made, part of the acid reacts with the more alkaline buffer to neutralize a portion of the acid and form the buffer salt from the acid in the process. Sodium carbonate or sodium orthophosphate, for example, could neutralize citric acid and form a buffer combination of citric acid and sodium citrate.

One preferred embodiment of the in-situ buffer system for a powdered, concentrated composition comprises using a carbonate salt as a buffer. When some of the acid is neutralized to form the corresponding buffer salt in situ, it is accompanied with the release of carbon dioxide as a by-product. The release of carbon dioxide can provide the beneficial function of a visually-perceptible signal that the solution is acidic and active. It can also be shown that the process of releasing carbon dioxide helps facilitate the dissolution of a powder concentrate and help disperse other functional additives.

Sodium carbonate, sodium bicarbonate, magnesium carbonate hydroxide, and mixtures thereof are preferred carbonate buffers.

The pH of the present composition is preferably greater than about 2, and especially does not contain large amounts of acid for consumer safety, especially when the compositions are not fully removed from the surface treated, especially food surfaces. If the composition has a pH of greater than about 5, the antimicrobial effectiveness of the composition is significantly diminished. If the pH of the present composition is less than about 2, the composition can have issues in regard to surface and human safety. The pH of the present compositions should typically be from about 2 to about 5, preferably from about 2.3 to about 3.5, and more preferably from about 2.5 to about 3.2.

Preferred effervescent buffers herein are selected from the group consisting of sodium carbonate, sodium bicarbonate, magnesium carbonate hydroxide, and mixtures thereof. The level of buffer used in the present concentrated compositions is typically from about 1% to about 60%, preferably from about 3% to about 30%, and more preferably from about 5% to about 15%, by weight of the concentrated composition. In dilute aqueous treatment compositions, the level of buffer is typically from about 0.0005% to about 3%, preferably from about 0.0015% to about 1.5%, and more preferably from about 0.0025% to about 0.75%, by weight of the dilute aqueous treatment composition.

In order to maintain the appropriate pH, the levels of both organic acid and buffer are typically carefully selected. If the levels of organic acid and buffer are not carefully selected, the resultant solution pH may be outside the desired range, or the buffering capacity of the solution at a preferred pH may be diminished limiting the robustness or microbial effectiveness of the cleaning solution. The present compositions preferably comprise organic acid and buffer in a ratio of organic acid to buffer of from about 100:1 to about 1:10, more preferably from about 50:1 to about 1:5, and even more preferably from about 20:1 to about 1:1.

E. Anti-Foaming Agent

At low levels, suds suppressors or anti-foaming agents can optionally be used in the present compositions, especially in the case where a certain surfactant level is desired for wetting and/or efficacy, but the degree of foam generated in the washing of, for example, produce is desired to be kept low. The amount of anti-foaming agent can be tailored in conjunction with the type and level of surfactant used.

Suitable anti-foaming agents include materials listed in the U.S. Code of Federal Regulations 21 CFR 173.340, which are hereby incorporated herein by reference.

Antifoam 2-4293 available from Dow Corning, and DC-4270 and DC2-4242 available from Dow Corning are useful anti-foaming agents herein.

Polypropylene glycol, as described hereinbefore as a stabilizing agent, can also, in addition to serving as a surfactant stability aid in solution, provide in-use foam control as well.

F. Perfume and/or Flavoring and Coloring Agents

Most hard surface cleaner products contain some perfume to provide an olfactory aesthetic benefit and to cover any "chemical" odor that the product may have. The main function of a small fraction of the highly volatile, low boiling (having low boiling points), perfume components in these perfumes is to improve the fragrance odor of the product itself, rather than impacting on the subsequent odor of the surface being cleaned. However, some of the less volatile, high boiling perfume ingredients can provide a fresh and clean impression to the surfaces, and it is sometimes desirable that these ingredients be deposited and present on the dry surface. For the purposes of the present invention, the term "perfume" is taken to include those ingredients which impart an aesthetic olfactory benefit. Such ingredients can include traditional perfumes, natural extracts, essences, and flavorings. The perfumes are preferably those that are more water-soluble and/or volatile to minimize spotting and filming. All of the perfumes useful in the present invention must be "food grade" or GRAS at the levels employed in order to be consistent with the essential character of the invention. Of particular usefulness are those perfumes which impart a citrus or lime character to the composition. Some of the perfumes useful herein are described in more detail in U.S. Pat. No. 5,108,660, Michael, issued Apr. 28, 1992, at col. 8 lines 48 to 68, and col. 9 lines 1 to 68, and col. 10 lines 1 to 24, said patent, and especially said specific portion, being incorporated by reference.

Flavoring agents can optionally be added as additional ingredients to further enhance the aesthetics of the product. Although normal usage of the present compositions on food surfaces would typically include a rinse step, there can instances where rinsing is not available or even desired (e.g. where the water might be contaminated). In this case, a flavoring agent or sweetening agent can be incorporated to smooth any tart taste that might accompany any residual acid on food surfaces.

Flavoring agents include those typically used in food and include extracts and artifical flavors. Vanilla, fruit flavors, and the like are preferred. Suitable sweetening agents for use in the compositions include natural and artificial sweeteners such as sucrose, fructose, dextrose, invert sugar, sorbitol, aspartame, saccharin.

Although a white color for solid products like powders and tablets has a clean perception to it, sometimes coloring agents may optionally be added to further enhance or differentiate the aesthetic appearance of the product. This is most common in the case of dilutable powders and tablets, but may also be used in liquids. Food grade coloring agents are the preferred materials. Coloring may range from a solid color for liquids and powders, to mixed colors in tablets and powders. Speckles in powders and tablets are also preferred. In general, when colors are used, the preferred colors are those colors which are seen in food like fruits and vegetables. Red like in apples, green like in limes or broccoli, orange like in oranges, yellow like in lemons are desired colors.

G. Other Optional Materials

In some instances optional material protection additives may provide a benefit. In the case where dilution water has a high chloride content, an acidic environment may cause an increase rate of corrosion on metal. Materials that can interact with the surface and provide material protection may be desired.

Process for Manufacturing Acidic Antimicrobial Compositions

The present acidic antimicrobial compositions can be manufactured by mixing together the various components of the composition. In general, any batch or continual powder mixing equipment can be used to manufacture the preferred powdered compositions of the present invention. For ease of processing, Ribbon mixers or Littleford mixers are preferred.

However, in the making of preferred concentrated, powdered compositions comprising an organic acid, carbonates, and liquid components, there are preferred processing techniques to achieve a stable and free-flowing powder composition. The addition of the liquid components, such as polypropylene glycol, polysorbates, flavoring agents, and the like, can increase the cohesiveness of powder mixes to the point where flowability of the mixture becomes problematic. In general, reducing the particle size of the dry (anhydrous) powder components, such as the acid, surfactant, or carbonate source, of the composition can help the flowability of the mix when liquid components cause flowability problems. Liquid components in some instances can also facilitate a slow reaction between organic acids and the carbonate source while the product is still in the dry concentrated form, manifested by the release of carbon dioxide gas. In order to prevent acid-carbonate reactions in the powder the preferred approach is to use a dense granular carbonate and coarse organic acid source in place of fine particle size material. This helps minimize the surface area of reactant species. Other dry, non-reactive, materials are then preferentially added with a finer particle size in order to adsorb the liquid to reduce overall product cohesiveness and further act as a barrier to inhibit the interaction between the acid and carbonate in the mix. In the event where the amount of the non-reactive materials available in the formula added as a finer powder for flowability is not sufficient to reduce cohesiveness, then some of the carbonate may be substituted for this purpose. In the case where use of reduced particle size carbonate is required, it is preferred that a less reactive form is used. Magnesium carbonate is preferred over sodium carbonate which is preferred over sodium bicarbonate. Other components that might negatively interact with the liquid, or are sensitive to shear in the making process, may preferentially be added last.

In a process for manufacturing a preferred concentrated, powdered composition of the present invention, the preferred order of addition of ingredients is: (1) an organic acid as the base which is then coated with the liquid components; (2) finely divided materials with smaller particle size to control cohesiveness and facilate separation of the acid from carbonate is then added to coat the organic acid-liquid mix; (3) if required, some ground carbonate, preferably a less reactive species, can be added; (4) the balance of the carbonate is then added along with other materials that might interact with the liquid, or be shear sensitive.

II. Article of Manufacture

The present invention also encompasses an article of manufacture for cleaning and treating food and/or food contact surfaces, comprising (a) a container, (b) an acidic antimicrobial composition, and (c) a set of instructions for use.

A. Container

Suitable containers for this invention include, for liquid concentrates, plastic bottles that facilitate pouring the product into a dosing container so as to comply with usage instructions, or a bottle that has a self contained dosing mechanism for ease of correct dosing. For tablets and powders, foil pouches and sachets are preferred. In the case where the tablet or powder composition includes carbonate sources, the pouches or sachets should provide a barrier, such as a foil seal, sufficient to prevent moisture from reaching the product which would cause a premature release reaction of $CO_2$. Packages of single use doses are particularly convenient here. In the case where an effervescent powder or tablet is packaged in multiple use containers, the containers should allow for resealing to keep moisture out and prolong product stability. A plastic container with a screw on or snap on lid is useful here.

B. Acidic Antimicrobial Composition

The present article of manufacture can comprise an acidic antimicrobial composition comprising an organic acid and surfactant, preferably anionic surfactant, as described hereinbefore. In a preferred embodiment, the present article comprises an acidic antimicrobial composition comprising an organic acid, anionic surfactant, and stablizing agent as described hereinbefore.

C. Set of Instructions

The present article of manufacture further comprises a set of instructions comprising an instruction to contact inanimate surfaces, preferably surfaces of food, more preferably surfaces of produce such as fruits and vegetables, with the acidic antimicrobial composition of present invention. The set of instructions can comprise instruction(s) to carry out the methods described hereinafter. The set of instructions are typically in association with the container of the present article. As used herein, the phrase "in association with" means the instructions are either directly printed on the container itself or presented in a different manner including, but not limited to, a brochure, print advertisement, electronic advertisement, and/or verbal communication, so as to communicate the set of instructions to a consumer of the article of manufacture.

When the present compositions are concentrated, dry or anhydrous powdered compositions, the set of instructions can further comprise an instruction to first dilute the powdered composition with water and then contact the surface to be treated. The instructions preferably instruct a consumer to dilute a concentrated, powdered composition with at least about 75 parts water, preferably at least about 95 parts water, and more preferably at least about 99.5 parts water.

III. Method of Use

In its broadest sense, the present method of cleaning and/or reducing microorganisms on a surface, especially food surfaces or food contact surfaces, comprises contacting the surface with an acidic antimicrobial composition comprising an organic acid and a surfactant, especially an anionic surfactant.

A preferred method of the present invention comprises contacting a surface, preferably a food surface or food contact surface, with an acidic antimicrobial composition comprising an acid, preferably an organic acid and a surfactant, preferably an anionic surfactant, and allowing the composition to remain on the surface for at least about 15 seconds, preferably at least about 1 minute, and more preferably at least about 5 minutes, before removing the composition, i.e. by rinsing or wiping the composition from the surface, in order to provide antimicrobial effectiveness on the surface. As used herein, "antimicrobial effectiveness" means that the total log reduction of microbes on a surface is at least about 1, preferably at least about 2, and more preferably at least about 3 log reduction.

The present methods preferably comprise contacting a surface with an acidic antimicrobial composition as described hereinbefore. Wherein the acidic antimicrobial composition is a concentrated composition, the method can further comprise diluting the concentrated composition with a solvent comprising water to form a diluted aqueous treatment composition, wherein the concentrated composition is diluted with enough solvent in order to provide organic acid at a level of from about 0.0025% to about 4.75%, preferably from about 0.15% to about 4.25%, and more preferably from about 0.03% to about 4%, and surfactant at a level of from about 0.0005% to about 5%, preferably from about 0.002% to about 2%, and more preferably from about 0.003% to about 1%.

The present invention also encompasses a method of promoting the sale of food items, including produce such as fruits and vegetables, which generally comprises contacting the food items (as described hereinbefore) with an acidic antimicrobial composition comprising an organic acid and surfactant, preferably the present acidic antimicrobial compositions, and providing informational indicia, such as an advertisement, logo, brochure, sticker, sign, or other printed matter, in association with said food items to indicate/communicate to a consumer of the food items that the food items have been treated with the acidic antimicrobial composition. Providing the informational indicia is an important element of the present method since communicating such information to a consumer allows the consumer to have confidence that the food items, especially produce such as fruits and vegetables, have reduced levels of pesticides, waxes, bacteria, and the like. Indeed, consumers who otherwise would not consume or purchase food items that have not been treated with a composition to clean and reduce microorganisms on the food items, would be influenced to consumer or purchase the food items when the fact that the items have been treated is communicated to the consumer.

A non-limiting example of such informational indicia is a sign comprising a brand name of the acidic antimicrobial composition used to treat the food items, wherein the sign is displayed in association with the food items treated. In this example, the consumers can easily determine that the food items have been treated and are therefore safe for human consumption.

The following are non-limiting examples of the present invention.

EXAMPLE I

This Example shows the antimicrobial efficacy of various acidic compositions. Compositions A,B,C and D are concentrated, powdered compositions and are diluted with water per the specified dilution factor (grams/Liter) to form a dilute aqueous treatment composition. The dilute aqueous treatment compositions are then evaluated in a standard suspension test for antimicrobial efficacy on *E.Coli* and *Staph. Aureus*. The suspension test used is the Modified AOAC Germicidal and Detergent Sanitizing Action Test.

| Component | A Wt % | B Wt % | C Wt % | D Wt % |
|---|---|---|---|---|
| Citric acid | 66.6 | 57.7 | 68.7 | 33.3 |
| Sodium citrate hydrous | 28.3 | 24.5 | 29.2 | 50.0 |
| Sodium lauryl sulfate | 5.1 | 17.8 | 2.1 | 16.7 |
| Total grams/Liter | 4.88 | 5.63 | 4.73 | 6 |
| sol'n pH | 3.5 | 3.5 | 3.3 | 4.5 |

Antimicrobial efficacy of samples A,B,C & D diluted in 1 Liter purified water. Data represents total Log Reduction at a given time.

| | A | B | C | D |
|---|---|---|---|---|
| *E. Coli* | | | | |
| 30 sec. | 1.13 | >7 | 5.7 | 0 |
| 1 min. | >7 | >7 | 5.11 | 0 |
| 5 min. | >7 | >7 | >7 | 0.58 |
| 10 min. | >7 | >7 | >7 | 0.85 |

| | A | B | C | D |
|---|---|---|---|---|
| *Staph. Aureus* | | | | |
| 30 sec. | >7 | >7 | 0.7 | >7 |
| 1 min. | >7 | >7 | 2.43 | >7 |
| 5 min. | >7 | >7 | >7 | >7 |
| 10 min. | >7 | >7 | >7 | >7 |

EXAMPLE II

The following Example demonstrates that an acid-anionic composition with the stabilizing agent polypropylene glycol (e.g. PPG 2000) retains antimicrobial effectiveness on produce (broccoli) that would be difficult to effectively wet in hard water without the stabilizing agent.

| Component | E Wt % | F Wt % |
|---|---|---|
| Citric Acid | 75.6 | 77.9 |
| Sodium Carbonate | 5.18 | 5.3 |
| Sodium Bicarbonate | 0.48 | 0.5 |
| Magnesium Carbonate | 2.04 | 2.0 |
| Sodium Lauryl Sulfate | 12.08 | 10.0 |
| PPG 2000 | 4.0 | 3.2 |
| Anti-foam Agent | 0.52 | 1.0 |
| Grapefruit Oil | 0.1 | 0.1 |

Concentrated powdered compositions E and F are prepared and dissolved in deionized and hard water (10 gpg) at a level of 5 grams of composition per Liter of water to form a dilute aqueous treatment composition. The dilute aqueous treatment compositions are then tested on broccoli samples for antimicrobial effectiveness.

A Broccoli sample is innoculated with a bacterial solution containing $\geq 10^8$ cfu bacterium per ml. Application of 100 microliters of this solution to the surface results in approximately $10^6$ to $10^7$ cfu per broccoli piece. Equal amounts of small spots are deposited to facilitate drying. After 30 minutes dry time the sample is placed in 50 ml of the dilute aqueous treatment composition for a 5 minute soak. After the 5 minute soak the sample is transferred to 50 ml of a neutralizer before being stomached for 2 minutes and subsequently plated to enumerate the organisms surviving the treatments. Suprisingly the acid-anionic system maintained equal or better antimicrobial activity vs. 200 ppm hypochlorite bleach over the range from 0 to 10 gpg, as shown by the data in the following Tables.

| | | Log Reduction in 5 minutes | |
|---|---|---|---|
| | | Staph aureus | E-Coli |
| Composition E | 0 gpg | 1.8 | 1.6 |
| | 10 gpg | 1.8 | 1.3 |
| 200 ppm NaOCl | 0 gpg | 1.5 | 1.2 |
| | 10 gpg | 1.3 | 1.3 |

|  | | Log Reduction (greater than water alone) in 5 minutes | |
|---|---|---|---|
|  | | Staph aureus | E-Coli |
| Composition F | 0 gpg | 1.38 | 1.19 |
|  | 10 gpg | 1.37 | 0.90 |
| 200 ppm NaOCl | 0 gpg | 1.08 | 0.86 |
|  | 10 gpg | 0.89 | 0.93 |

Composition E is further tested on *Salmonella* and *Listeria* on broccoli with similar results.

|  | | Log Reduction (greater than water alone) in 5 minutes | |
|---|---|---|---|
|  | | Salmonella | Listeria |
| Composition E | 0 gpg | 1.07 | 1.26 |
| 200 ppm NaOCl | 0 gpg | 0.67 | 0.77 |

EXAMPLE III

An acid-anionic system with stabilizing agent Tween™ 81 is evaluated for the effect of adding a carbonate source in a table form for improved dissolving. The carbonate source is calculated to give the same acid-buffer ratio in solution as the citric acid/sodium citrate version.

| Component | G Wt % | H Wt % |
|---|---|---|
| Citric acid | 70.87 | 75.67 |
| Sodium citrate | 17.72 | — |
| Sodium bicarbonate | — | 13.85 |
| Sodium lauryl sulfate | 8.81 | 8.09 |
| Tween 81 | 1.80 | 1.66 |
| Antifoam | 0.80 | 0.74 |

The compositions G and H are made and each pressed into a 5 gram tablet. Each tablet is subsequently dropped into 1 liter of tap water and observed for rate of dissolution by visual appearance and tracking pH drop. When dropped in water, composition H has effervescence action that helps to dissolve the composition, while composition G has none. Composition H is essentially fully dissolved at 6.5 minutes and composition G is only partially dissolved within the same time frame. The pH of H at 6.5 minutes is 2.96, while the pH of G is 6.6. The approach of using excess acid to react with a carbonate source to form the acid/acid salt buffer system gives a noticeable dissolving improvement.

EXAMPLE IV

Compositions I and J are diluted with water having medium and high hardness to determine the effect of the stabilizing agent polypropylene glycol (e.g. PPG 2000).

| Component | I Wt % | J Wt % |
|---|---|---|
| Citric acid anhydrous | 77.6 | 80.33 |
| Sodium Carbonate | 7.6 | 7.87 |
| Sodium Lauryl Sulfate | 10.4 | 10.77 |
| PPG 2000 | 3.4 | — |
| Antifoam 2-4293 | 1 | 1.03 |
| Total gm dosed | 5.0 | 4.83 |

Compositions I and J are prepared and diluted in 1 liter of water having 20 grains per gallon hardness. After 10 minutes, samples of fresh broccoli heads are submerged in each of the solutions for 10 seconds and then removed from the solution and observed to determine the wetting ability of each composition. The composition I solution visually wetted better and gave a greener appearance vs. the composition J solution. After 20 additional minutes, fresh broccoli is dipped for 10 seconds with the same results that is observed at 10 minutes.

A repeat of compositions I and J are made. These compositions are dissolved in 2 liters of water having about 8 grains per gallon hardness at a nominal concentration of 2.5 g/L. As above, fresh broccoli heads are dipped in both solutions for 10 seconds and then observed for wetting ability of each composition. The composition I solution visually wetted better than the composition J solution and was visually greener in appearance.

EXAMPLE V

The following compositions K and L are diluted with water having high hardness to determine the effect of the stabilizing agent polypropylene glycol (e.g. PPG 2000) on broccoli cleaning and wetting.

| Component | K Wt % | L Wt % |
|---|---|---|
| Citric acid anhydrous | 62.1 | 60.9 |
| Sodium Citrate hydrous | 32 | 31.3 |
| Sodium Lauryl Sulfate | 5.9 | 5.8 |
| PPG 2000 | — | 2 |
| Total gm dosed in 1 Liter | 5.47 | 5.58 |

Compositions K and L are dissolved in 1 liter of hard water (having a hardness of 19.5 grains per gallon). After 10 minutes, broccoli heads are dipped into each solution for 10 seconds, then rinsed with tap water and evaluated for wetting and color change. The composition K solution had minimal wetting and color change, while the composition L solution had visually good wetting and a darker green appearance indicating a cleaner surface.

EXAMPLE VI

The following example shows the beneficial effect of a stabilizing agent polypropylene glycol (e.g. PPG 2000) when added to a citric acid and sodium lauryl sulfate composition. Solution contact angle expansion is observed when the stabilizing aid is removed.

| Component | M Wt % | N Wt % |
|---|---|---|
| Citric acid anhydrous | 85.91 | 84.16 |
| Sodium Carbonate | 8.43 | 8.25 |
| Sodium Lauryl Sulfate | 5.66 | 5.45 |
| PPG 2000 | | 2.04 |
| Total gm dosed in 1 Liter | 4.56 | 4.65 |

The purpose of this example is to examine the stabilizing effect the addition of polypropylene glycol (e.g. PPG 2000) has on the contact angle of the diluted aqueous treatment solution in medium hardness water at room temperature (72° F.).

To facilitate having the concentrated, powdered compositions M and N fully dissolved for an initial reading of contact angle (within 10 sec. of making the full solution), the compositions are first fully dissolved in 600 ml of deionized water. Once fully dissolved, 400 ml of hard water (having about 19.5 grains per gallon) is poured into the 600 ml solution raising the total solution size to 1 liter and the total hardness to about 7.8 grains per gallon. The solution is then sampled with a positive displacement pipette using a volume of 10 micro-liters. This sample volume is then placed on a flat hydrophobic surface (i.e. Reynolds Cut-Rite wax paper) forming a droplet on the surface. The drop is then photographed with a digital camera. A print out of the picture is then measured for the drop height (h) from the surface and diameter (d) where it intersects the surface to determine the approximate contact angle. For this estimate, the contact angle is calculated from the equation: $\theta = \text{Arctan}(4dh/[d^2 - 4h^2])$.

| Contact Angle (Degrees) vs. Solution Age After Making (Minutes) | | | | | |
|---|---|---|---|---|---|
| | Initial | 1 minute | 5 minutes | 10 minutes | 30 minutes |
| M | 53.8° | 55.3° | 61.7° | 70.9° | 64.7° |
| N | 52.2° | 51.6° | 54.7° | 58.4° | 52.5° |

At the end of this test, a section of a broccoli head is dipped in each solution for 10 seconds and then rinsed with tap water. The section that was washed was compared to an unwashed piece of broccoli for appearance. The composition M solution showed minimum difference from unwashed broccoli, while the composition N solution showed good wetting as indicated by more solution draining out of the cluster when removed from the solution as well as a change in color to a deeper green indicating good surface wetting and better cleaning.

EXAMPLE VII

The following example shows the beneficial effect of a stabilizing agent polypropylene glycol (e.g. PPG 2000) when added to a citric acid and sodium lauryl sulfate formula. Solution contact angle is observed using compositions with and without the stabilizing agent.

| Component | O Wt % | P Wt % |
|---|---|---|
| Citric acid anhydrous | 81.3 | 78.2 |
| Sodium Carbonate | 7.9 | 7.6 |
| Sodium Lauryl Sulfate | 10.8 | 10.4 |
| PPG 2000 | | 3.8 |
| Total gm dosed in 1 Liter | 4.82 | 5.01 |

The purpose of this example is to examine the stabilizing effect the addition of PPG 2000 has on the contact angle of a diluted aqueous treatment solution in medium hardness water at room temperature (72° F.).

To facilitate having the composition fully dissolved for an initial reading of contact angle, the compositions O and P are first fully dissolved in 1000 ml of deionized water. Once fully dissolved, diluted aqueous treatment solution is sampled with a positive displacement pipette using a volume of 10 micro-liters. This sample volume is placed on a flat hydrophobic surface (i.e. Reynolds Cut-Rite wax paper) forming a drop on the surface. The drop is photographed with a digital camera after 20 seconds. A print out of the picture is then measured for the drop height (h) from the surface and diameter (d) where it intersects the surface to determine the approximate contact angle, as described in Example VI. After the initial measurements, 4 grams of water hardness concentrate is added to the initial solutions. This is calculated to add about 11 grains per gallon hardness to the solutions. The solutions are mixed and after sitting 10 minutes are sampled as above to determine the contact angle.

| Contact Angle (Degrees) vs. Solution Age After Making (Minutes) | | |
|---|---|---|
| | Initial | 10 minutes |
| O | 56.3° | 64.1° |
| P | 56.3° | 54.1° |

EXAMPLE VIII

This example shows the benefits of a stabilizing agent in an acid/anionic composition can be achieved via a separate dosing from a primary composition Q that does not comprise a stabilizing agent.

| Component | Q Wt % |
|---|---|
| Citric acid anhydrous | 20.6 |
| 50% NaOH | 3.6 |
| Sodium Lauryl Sulfate | 4.39 |
| DI water | 71.37 |
| Total gm dosed in 1 Liter | 10 gm |

250 grams of a liquid concentrate composition Q is made as indicated in the table above. Two 10 gram samples of composition Q are sampled and prepared to be added into a 1 liter beaker containing medium hardness (about 7 grains per gallon) tap water. In one of the 1 liter water samples, before the concentrated composition Q is added, 2 grams of a stability agent (e.g. magnesium sulfate heptahydrate) is dissolved. Following the addition of the stability agent to the water solution, the composition Q is introduced and stirred in. Composition Q is also added to a 1 liter beaker with water having no stabilizing agent added. The solutions in the beakers are evaluated after 20 minutes for stability. The solution comprising the magnesium sulfate heptahydrate is clear and homogeneous while the solution without the stabilizing agent has obvious precipitation.

This experiment demonstrates that a stabilizing agent can be added separate from the primary composition to achieve the same effect as if it were included with the composition itself.

EXAMPLE IX

This example illustrates a process for manufacturing a preferred stable, free-flowing effervescent, powdered acidic antimicrobial composition of the present invention that comprises organic acid and carbonate sources with a liquid component as described by the following:

(a) An organic acid is added with a preferred mean particle size distribution of 400–600 microns.

(b) Slowly adding the liquid component to the dry acid powder until the liquid is uniformly distributed. At this point the mass may be cohesive by nature and may require addition of a flow aid agent.

(c) Mixing flow aid agent, preferably not the alkali metal carbonate, having a mean particle size of less than 100 micron to provide flowability and serve as a barrier to the acid source.

(d) Mixing in the alkali metal carbonate. Use of a dense carbonate is preferred to achieve acceptable effervescence stability. Some smaller particle size carbonate may be utilized to provide acceptable granule flowability. A particle size reduction to a mean particle size of less than 50 microns is preferred. Use of light magnesium carbonate is preferred in this case for stability and flowability.

(e) Adding the remaining dry material in the granulation process. Final addition of some finely divided powder material may additionally help flowability. Finely divided dry surfactant materials like sodium lauryl sulfate that is shear sensitive or which interacts with the liquid components under shear are preferentially added last to improve product flowability. Other shear sensitive materials like antifoam compounds are also added last.

What is claimed is:

1. A stabilized, concentrated, acidic antimicrobial composition that forms a substantially clear diluted aqueous composition upon dilution, said stable, concentrated, acidic antimicrobial composition comprising:

(a) from about 60% to about 80%, by weight of said concentrated composition, of an organic acid;

(b) from about 1% to about 80%, by weight of said concentrated composition, of $C_6$–$C_{18}$ alkyl sulfate surfactant;

(c) polypropylene glycol;

(d) a member selected from the group consisting of sodium carbonate, sodium bicarbonate, magnesium carbonate hydroxide and magnesium carbonate;

(e) optionally, toxicologically-acceptable anti-foaming agent;

(f) optionally, toxicologically-acceptable preservative;

(g) optionally, perfume, flavoring agent, and/or coloring agent; and (f) the balance comprising compatible, toxicologically-acceptable inert and/or minor ingredients;

wherein said concentrated composition has a pH of from about 2 to about 5 upon dilution; and wherein the ratio of said polypropylene glycol to said surfactant is from about 10:1 to about 1:10 to about 10:2.

2. The concentrated composition of claim 1, wherein said surfactant is sodium lauryl sulfate.

3. The concentrated composition of claim 1, wherein said surfactant is present at a level of from about 4% to about 25%, by weight of said concentrated composition.

4. A process for manufacturing a stable, concentrated, acidic antimicrobial composition according to claim 1 that forms a substantially clear diluted aqueous composition upon dilution, said composition comprising said organic acid, $C_6$–$C_{18}$ alkyl sulfate in powdered form, carbonate source, anti-foaming agent, and polypropylene glycol, said process comprising:

(a) placing said organic acid having a mean particle size distribution of from about 400 to about 800 microns in a mixing vessel;

(b) slowly adding said polypropylene glycol to said organic acid until said polypropylene glycol uniformly distributed;

(c) mixing in said powdered surfactant having a mean particle size of from about 10 to about 150 microns;

(d) mixing in said carbonate source having a mean particle size of from about 100 to about 600 microns; and (e) mixing in said anti-foaming agent at moderate shear to form a uniform mixture.

5. The process of claim 4, wherein said carbonate source is sodium carbonate.

6. The process of claim 4, wherein said organic acid is citric acid and said powdered surfactant is sodium lauryl sulfate.

7. The process of claim 5, wherein said process further comprises mixing in fine sodium carbonate having a mean particle size from about 5 to about 50 microns with granular sodium carbonate having a mean particle size of from about 100 to about 600 microns, wherein a ratio of said fine carbonate to said granular sodium carbonate is from about 1:100 to about 100:1.

8. The process of claim 5, wherein said process further comprises mixing in magnesium carbonate along with said sodium carbonate, wherein said magnesium carbonate has a mean particle size of from about 5 to about 50 microns and wherein a ratio of said magnesium carbonate to said sodium carbonate is from about 1:100 to about 100:1.

9. A stabilized, concentrated, acidic antimicrobial composition that forms a substantially clear diluted aqueous composition upon dilution, said stable, concentrated, acidic antimicrobial composition comprising:

(a) from about 60% to about 80%, by weight of said concentrated composition, of an organic acid selected from the group consisting of citric acid, lactic acid, malic acid, salicylic acid, acetic acid, adipic acid, fumaric acid, hydroxyacetic acid, dehydroacetic acid, glutaric acid, tartaric acid, fumaric acid, succinic acid, propionic acid, aconitic acid, sorbic acid, benzoic acid, gluconic acid, ascorbic acid, alanine, and lysine, and mixtures thereof;

(b) from about 1% to about 80%, by weight of said concentrated composition, of a surfactant selected from the group consisting of anionic surfactant, nonionic surfactant, and amphoteric surfactants, and mixtures thereof;

(c) from about 2% to about 20%, by weight of said stabilized composition, of polypropylene glycol;

(d) from about 1% to about 60%, by weight of said concentrated composition, of a buffer selected from the group consisting of sodium carbonate, sodium bicarbonate, magnesium carbonate hydroxide, and mixtures thereof;
(e) a toxicologically-acceptable anti-foaming agent;
(f) optionally, toxicologically-acceptable preservative;
(g) optionally, perfume, flavoring agent, and/or coloring agent; and
(h) the balance comprising compatible, toxicologically-acceptable inert and/or minor ingredients;

wherein said concentrated composition has a pH of from about 2 to about 5 upon dilution; and wherein a ratio of said polypropylene glycol to said surfactant is from about 10:1 to about 1:20.

10. A method of cleaning and/or reducing microorganisms on a food surface of food contact surface comprising contacting said surface with an acidic antimicrobial composition according to claim 9 diluted in water.

* * * * *